US005853426A

United States Patent [19]
Shieh

[11] Patent Number: 5,853,426
[45] Date of Patent: Dec. 29, 1998

[54] METHOD AND APPARATUS FOR DELIVERING ATRIAL DEFIBRILLATON THERAPY WITH IMPROVED EFFECTIVENESS

[75] Inventor: Mae-Mae Shieh, Palo Alto, Calif.

[73] Assignee: Pacesetter, Inc., Sunnyvale, Calif.

[21] Appl. No.: 867,318

[22] Filed: Jun. 2, 1997

[51] Int. Cl.$^6$ .................................................. A61N 1/39
[52] U.S. Cl. ................................................................ 607/5
[58] Field of Search ........................................ 607/4, 5, 14

[56] References Cited

U.S. PATENT DOCUMENTS

| | | | |
|---|---|---|---|
| 5,107,850 | 4/1992 | Olive | 600/518 |
| 5,265,602 | 11/1993 | Anderson et al. | 607/9 |
| 5,350,404 | 9/1994 | Adams et al. | 607/5 |
| 5,431,689 | 7/1995 | Weinberg et al. | 607/14 |
| 5,500,008 | 3/1996 | Fain | 607/5 |
| 5,509,925 | 4/1996 | Adams et al. | 607/5 |
| 5,531,767 | 7/1996 | Fain | 607/5 |
| 5,545,182 | 8/1996 | Stotts et al. | 607/5 |
| 5,549,641 | 8/1996 | Ayers et al. | 607/4 |
| 5,591,215 | 1/1997 | Greenhut et al. | 607/14 |

OTHER PUBLICATIONS

U.S. Patent Application No. 08646409, "Method and Apparatus for Delivering Defibrillaton Shocks with Improved Effectiveness", Bush, et al.

"Epidemiology and Mechanism of Atrial Fibrillatin and Atrial Flutter", Camm, et al, *The American Journal of Cardiology*, vol. 78 (8A), Oct. 17, 1996.

"Fourier Analysis of Ventricular Fibrillation and Synchronization of DC Countershocks in Defibrillation" Carlisle, et al, *Journal of Electrocardiology*, 1988, 21:337–343.

"The Minimal Energy Requirment for Transthoracic Cardioversion of Various Types of Atrial Fibrillation", Daoud, et al, *Journal of American College of Cardiology*, Abstract 1020–10, Feb. 1996.

"Shocks Synchronized with Activations Passing Through an Anatomical Isthusm Reduce Atrial Cardioversion Threshold—a Computer Modeling Study", Ellis et al, Circulation, vol. 94 No. 8, Oct. 15, 1996.

"Do Unsuccessful Subthreshold Defibrillation Shocks Enable Subsequent Sucessful Defibrillation with Lower Energy?", Heinz, et al, *Journal of American College of Cardiology*, Feb. 1996, 328A.

"Genesis of Sigmoidal Dose–response Curve During Defibrillation by Random Shook . . .", Hsia, et al, *Pace,* vol. 13, Oct. 1990 pp. 1326–1342.

"On–Line Electronic Identification of a Period of Vulnerability to Defibrillaton . . . ", Hsia, et al, *Am. Heart Association conf. in Atlanta,* Abstract, Nov. 1993.

"A Critical Period of Ventricular Fibrillation more Susceptible to Defibrillation . . . " Hsia, et al, *Pace,* vol. 19, Part I, Apr. 1996, pp. 418–438.

"Improved Nonthoracotomy Defibrillation Based on Ventrivular Fibrillation Waveform Characteristics", Hsia, et al, *Pace,* vol. 19, Nov. 1996.

(List continued on next page.)

*Primary Examiner*—Jeffrey R. Jastrzab
*Attorney, Agent, or Firm*—Steven M. Mitchell

[57] ABSTRACT

A method for defibrillating a patient's atria with an implantable defibrillator having defibrillation synchronized to the atrial fibrillation waveform. The defibrillator is used to detect fibrillation in a patient's aria, monitor at least one atrial fibrillation signal across two electrodes, then deliver a high energy shock during a period of atrial fibrillation when the cycle lengths are stable within a desired measure of the cycle lengths monitored during the monitoring time period. The shock is then delivered synchronous with the R wave to avoid inducing ventricular fibrillation. The defibrillator also includes a timer so that if the desired cycle length stability is not reached within a specified time limit, the shock will be delivered with less stringent cycle length stability criteria.

22 Claims, 9 Drawing Sheets

OTHER PUBLICATIONS

"Effect of Shock Timing on the Probability of Successful Defibrillation", *Pace* vol. 19, Part II, Apr. 1996, pp. 735.

"Low–Energy Synchronous Cardioversion of Ventricular Tachycardia using a Catheter Electrode . . . " Jackman, et al, *Circulation,* 1982, 66:187–195.

"Ventricular Fibrillaton: The Importance of Being Course?", Jones, et al, *Journal of Electrocardiology,* 1984, 17:393–399.

"Effect of Right Atrial Linear Lesions on Atrial Defibrillations Threshold. Implication for Hybrid Therapy", Kalman, et al, *Pace,* 1996.

"Impact of Pulse Characteristics on Atrial Defibrillation Energy Requirements", Keane, *Pace* vol. 17, Part II, May 1994, pp. 1048–1057.

"Integration of Absolute Ventricular Fibrillation Voltage Correlates with Successful Defibrillation", Kuelz, et al, *IEEE Trans. Biomedical Eng.,* vol. 41, No.8, Aug. 1994, pp. 782–791.

"Synchronization of Low–Energy Pulses to Rapid Deflection Signals as a Possible Mechanism of Subthreshold Ventricular Defibrillaton", Mower, et al, *Circulation,* 1982, 66 Suppl. II:II–75.

"An Analysis of Spatiotemporal Activation Patterns to Identify Local Streaming of Wavefronts during Atrial Fibrillation in dogs", Steiner, et al, *Circulation,* vol. 94, No. 9, Oct. 15, 1996, #2048.

"Regional Anatomic Differences in Atrial Fibrillaton Organization in the Canine Right Atrium", Steiner, et al, *Circulation,* vol. 94, No. 8, Oct. 15, 1996, #2053.

"The Alternation Between Atrial Flutter and Atrial Fibrillation", Turnick, et al, *Chest,* 1992, 101:34–36.

"Atrial Flutter, Advances in Mechanisms and Management", Waldo, et al, Futura Publishing Co., Inc., Armonk, NY, 1996, pp. 389.

METHOD AND APPARATUS FOR DELIVERING ATRIAL DEFIBRILLATON THERAPY WITH IMPROVED EFFECTIVENESS

FIELD OF THE INVENTION

The present invention relates generally to implantable cardiac stimulation devices, and more specifically to an implantable defibrillator that delivers energy for termination of atrial fibrillation or atrial flutter.

BACKGROUND OF THE INVENTION

Following detection of ventricular fibrillation (VF), prior art implantable cardioverter defibrillators (ICD) typically deliver a defibrillation shock as soon as their high voltage capacitors are charged, and in more advanced systems, after VF is reconfirmed. Unlike VF, atrial fibrillation (AF) is not immediately life-threatening. In fact, at least several minutes can pass prior to therapy delivery without any ill effects. This time can be used to monitor the heart for conditions that would be more susceptible to atrial defibrillation; then, the arrhythmia can be terminated using a lower energy than would typically be used were the therapy delivered at a random time in AF.

As used herein, the word "atrial fibrillation" (AF) may be used to refer to atrial fibrillation, atrial flutter, or both, unless otherwise specified. As used herein, the word "atrial defibrillation" may be used to refer to termination of atrial fibrillation, atrial flutter, or both, using antitachycardia pacing, other pacing therapies/schemes, or high or low energy shocks (also referred to as "cardioversion"), unless otherwise specified.

It is desirable to reduce the size of an ICD in order to improve patient comfort, reduce risk of erosion through the skin, and facilitate pectoral placement. Because the batteries and capacitors account for a large portion of the defibrillator, reducing the defibrillation threshold (DFT), or the amount of energy, voltage, or current required to defibrillate the heart, is key to allowing the device size to be reduced. Using less energy to defibrillate has the added benefit of improving patient comfort and reducing trauma to the patient's cardiac conduction system, as well as prolonging battery and device life.

It has been observed that the energy and current required to electrically cardiovert atrial flutter is less than to cardiovert atrial fibrillation, and that, in general, "less organized tachycardias require more energy and current to terminate" (Waldo AL, Touboul P (eds): *Atrial Flutter: Advances in Mechanisms and Management*, Armonk, N.Y.: Futura Publishing Company, Inc., 1996, p. 389). There also have been observations that atrial fibrillation and atrial flutter coexist in the same patient, and the patient's rhythm may alternate between the two (Camm et. al., JACC Vol. 78 (8A), Oct. 17, 1996. p. 7). Given these observations, it is likely that shocking during these periods of atrial flutter may result in easier conversion to normal sinus rhythm (NSR).

An electrogram is sensitive to the location of the electrodes from which it is sensed. Electrodes that are at least 3 centimeters apart provide a relatively global atrial fibrillation signal, referred to as "unipolar", or "far-field", and may provide information indicating the proportion of the heart that is depolarized. Closely-spaced electrodes provide a "bipolar" signal that gives information regarding only the AF wavefronts passing through the localized area between the two electrodes. The amplitude of the signal depends, in part, on the direction the wavefront is traveling; the signal will be largest when traveling parallel to the two electrodes, and smallest when perpendicular to them. This signal can be monitored while the high voltage capacitors are charging. When the capacitors are fully charged, the shock can be delivered during a period of AF when the AF cycle lengths (CL) are within a desired measure of each other. Regularity of AFCL may imply organization of the wavefront, which may indicate a more re-entrant mechanism for the rhythm, as compared with rhythms of less stable AFCL.

In "Genesis of Sigmoidal Dose-Response Curve During Defibrillation by Random Shock: A Theoretical Model Based on Experimental Evidence for a Vulnerable Window During Ventricular Fibrillation," in *PACE* 1990, 13:1326–1342, Hsia et al. discuss a theoretical model and experimental results for using a surface electrocardiogram (ECG) to identify a window of VF during which the ventricles are more susceptible to defibrillation. In their experiments, they compared the VF waveform voltage at the time of shock delivery for successful and unsuccessful shocks. The shock strength was held constant, and was chosen to produce a defibrillation success rate of 50%. When using a recording from a lead II surface ECG, the absolute VF voltage (AVFV) was found to exhibit significantly larger values for successful defibrillation as compared to unsuccessful defibrillation. The mechanism for higher defibrillation success rate during large amplitude signals is not clear.

In U.S. Pat. Nos. 5,500,008 and 5,531,767 to Fain, which are assigned to the assignee of the present invention and incorporated herein by reference, a far-field fibrillation voltage is monitored across two spaced-apart implanted electrodes. Then a high energy shock is delivered during a period of ventricular fibrillation when the absolute values of he peak and trough voltages exceed a threshold based on a desired percentage greater than a running average of the absolute values of the peaks and troughs of the monitored fibrillation voltages.

In "Impact of Pulse Characteristics on Atrial Defibrillation Energy Requirements," Keane suggests that if the existence of a similar vulnerable window were revealed for atrial defibrillation, atrial defibrillation shocks could be delivered when the wave coincides with a peak in absolute atrial fibrillation voltage.

SUMMARY OF THE INVENTION

The present invention is directed toward the provision of a defibrillator that increases the likelihood for successful atrial defibrillation at any particular shock strength by delivering the defibrillation pulse during a period corresponding to stable AFCL as monitored by at least one electrogram during AF. Multiple electrograms (any combination of bipolar or far-field electrograms available) may be monitored simultaneously for these stable periods.

The implantable defibrillator of the present invention reduces the atrial defibrillation threshold (ADFT) by delivering a defibrillation shock during a period of AF when the atria are more susceptible to defibrillation. AF has been observed to oscillate among very disorganized, more organized, and atrial flutter-like periods. Atrial flutter or flutter-like rhythms also appear to be more easily defibrillated than periods of more disorganized atrial fibrillation. Therefore, the target time of atrial defibrillation shock delivery should be when the rhythm is atrial flutter, or at least when the rhythm is more organized. Sensing is used to provide an electrogram that is monitored during AF to determine a time when the stability of the AFCL meets certain preset criteria.

More than two electrodes may be used in combination to generate the AF sensed signal or signals. Two pairs of electrodes may be used, with or without one electrode in common, to observe fibrillation wavefronts from two directions or in different areas of the atrium.

A ventricular signal is monitored to synchronize atrial defibrillation energy delivery with a ventricular depolarization of a sufficiently large preceding cycle length, such as greater than 400 ms, to avoid inducing ventricular fibrillation.

In a preferred embodiment, the electrodes used for atrial and/or ventricular monitoring are on the same leads used to deliver the high energy atrial defibrillation shock. This is advantageous since no extra leads are required, and the present invention can be used with existing lead systems.

A timer is included in the defibrillator so that if a period of stable AFCL is not obtained within a certain time, say 45 minutes from the detection of AF, the cycle length stability criteria is lessened.

It is thus a primary object of this invention to provide an implantable cardiac defibrillator that delivers a defibrillation pulse at a time most likely to defibrillate the atria at the lowest energy.

BRIEF DESCRIPTION OF THE DRAWINGS

The various features and advantages of the present invention may be more readily understood with reference to the following detailed description taken in conjunction with the accompanying drawings in which.

DETAILED DESCRIPTION OF THE INVENTION

The present invention is directed toward the provision of a defibrillator that delivers a defibrillation shock to the heart during a window of AF in which the shock is likely to be successful in defibrillating the atria. Variation in the stability of the atrial arrhythmia results in a cyclic window of increased susceptibility to defibrillation. The susceptible window occurs when the AF cycle length is essentially constant, i.e., a more stable state.

Figure 1:
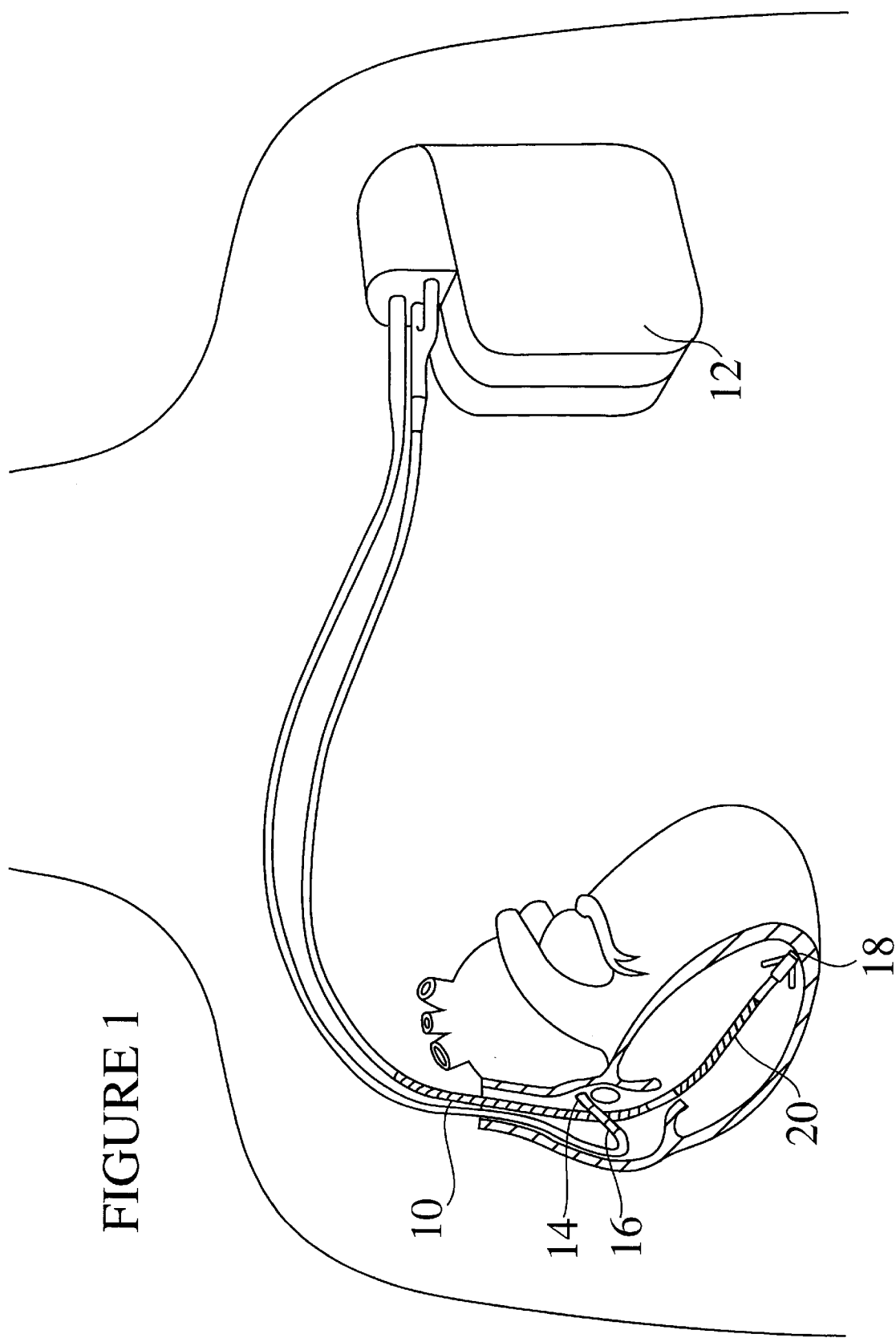
FIG. 1 is an illustration of an electrode system, including a superior vena cava (SVC) defibrillation electrode and an electrically active pulse generator case placed subcutaneously (SubQ) in the patient's left pectoral region for delivering defibrillation energy to the atria, and bipolar electrodes in the high right atrium (HRA) used to sense an atrial electrogram.

FIG. 1 is an illustration of a superior vena cava (SVC) defibrillation electrode 10 and an electrically active pulse generator (PG) case 12 located subcutaneously (SubQ) in the patient's left pectoral region for atrial defibrillation shocks. The pulse generator within PG case 12 may be similar to those known in the art, such as that described in U.S. Pat. No. 5,007,422 to Pless et al., which is assigned to the assignee of the present invention and incorporated herein by reference, with the addition of the special timing features of the present invention. Atrial tip electrode 14 and atrial ring electrode 16 are provided for sensing the bipolar (near-field) atrial electrogram to assess local organization. SVC electrode 10 and PG case 12 may be used for sensing a unipolar (far-field) atrial electrogram. Either or both of these sensing configurations may be used for determining the window of increased susceptibility to defibrillation. In the preferred embodiment, at least the bipolar signal is monitored from electrodes 14 and 16, and other signals may be added for additional information. Advantages of this configuration are that the electrodes are readily available and that there are minimal far-field R waves picked up to obscure the atrial signal.

An RV tip electrode 18 and RV sensing electrode 20 are provided for monitoring a ventricular electrogram. RV sensing electrode 20 may also be used for atrial and/or ventricular defibrillation, discharged against SVC defibrillation electrode 10, active PG case electrode 12, or both.

Figure 2A:
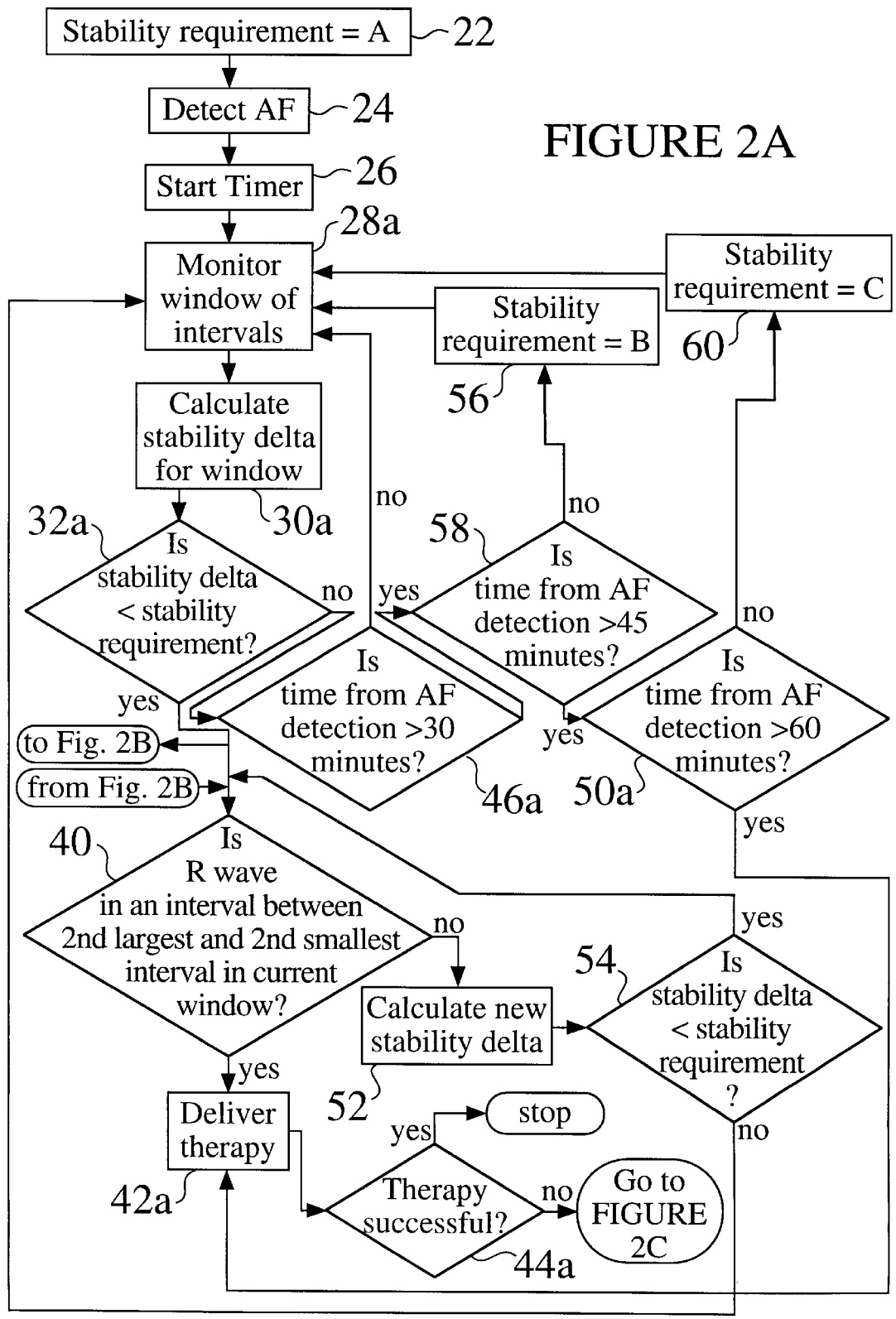
FIGS. 2A–C are schematic block diagrams of the logic and detection circuitry for processing electrograms in order to deliver defibrillation energy when the atria are most susceptible to being defibrillated.
Figure 2B:
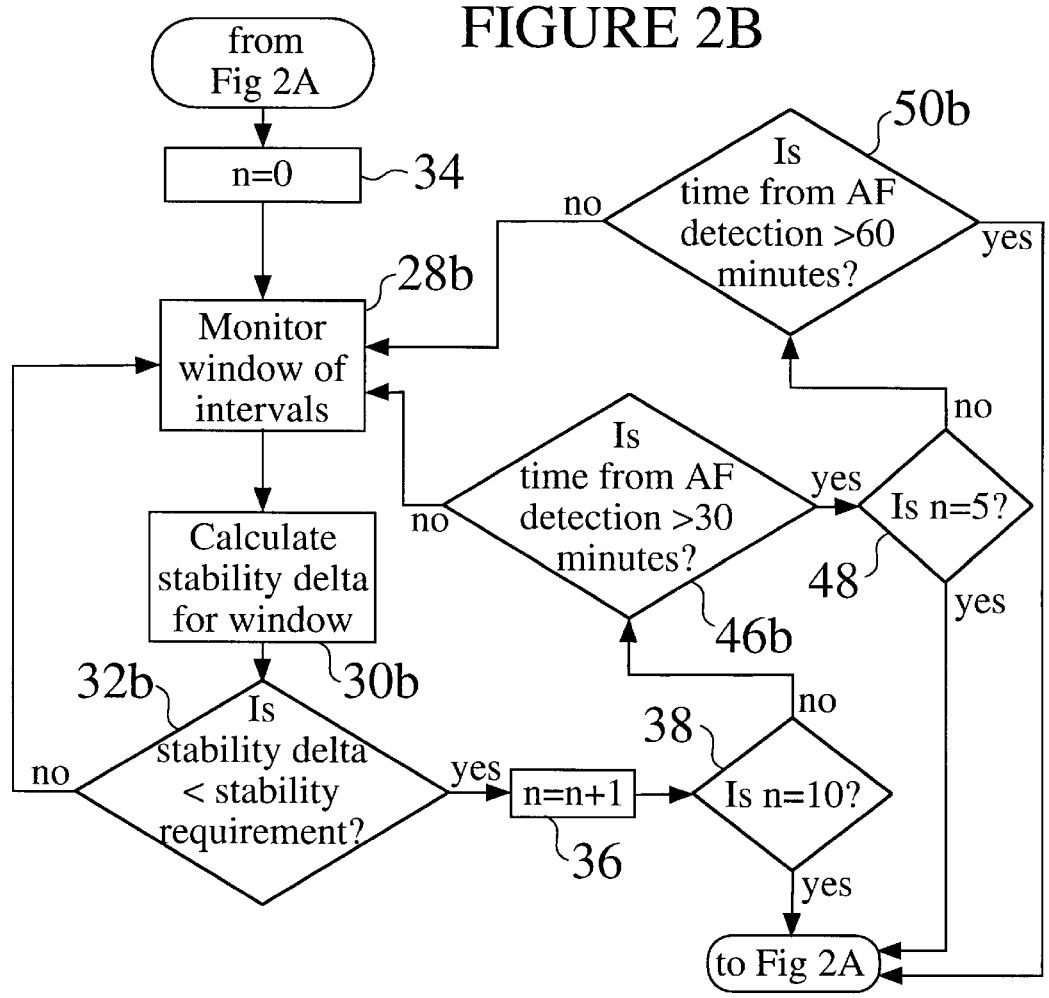
Figure 2C:
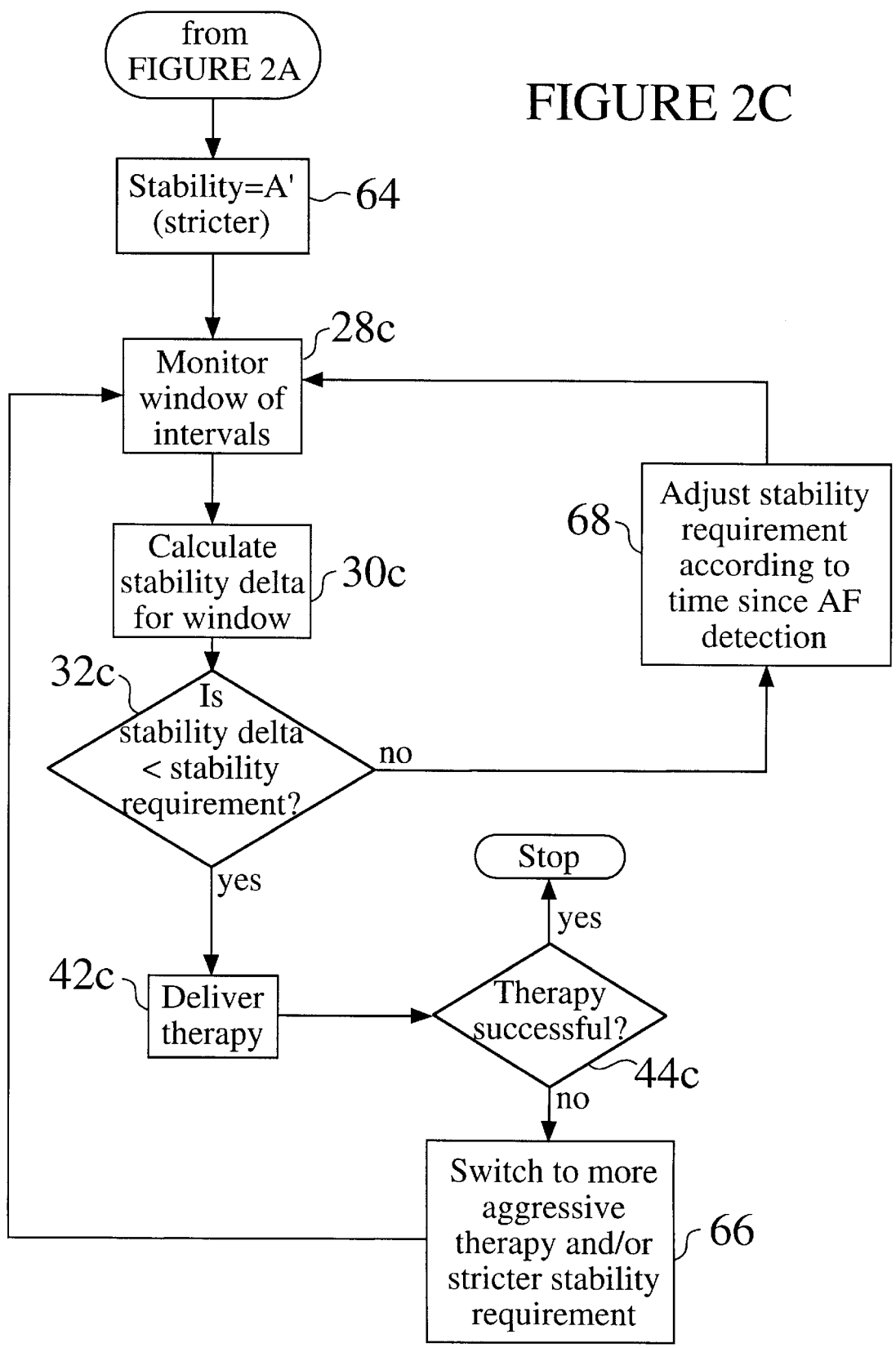

FIGS. 2A–C are schematic block diagrams of the steps performed by the logic and detection circuitry of the ICD for processing the atrial and ventricular electrograms in order to deliver defibrillation energy when the atria are most susceptible to being defibrillated. The amount of stability required before defibrillation delivery—the "stability requirement"—can be programmable by the user or based on analysis of the rhythm or both, as is the case in FIG. 2A. The first stability requirement, A, is programmed by the user in step 22. Following detection of AF in step 24, a timer is started in step 26. In the preferred embodiment, a window of 8 to 20 intervals is observed in step 24. To determine stability of intervals in step 30, the second smallest interval is subtracted from the second largest interval. This difference is called the stability delta. To facilitate this calculation, it is preferred that the detected signal be digitized early in the processing as is shown in U.S. Pat. No. 5,027,814 to Carroll et al., which patent is incorporated herein by reference. In step 32, this stability delta is compared with the preprogrammed stability requirement A. The rhythm may be considered stable when the stability delta is less than the designated cycle length stability requirement, which is preferably between 5 and 80 ms, and may be for example 20 ms.

Alternatively, instead of using a preset stability requirement A, the stability requirement may be based on stability deltas calculated for the windows of intervals monitored during a first monitoring time period of preferably 30 minutes or less from detection of AF. For instance, if the minimum stability delta seen during the first monitoring period is 35 ms, the stability requirement during a second monitoring period may be set to 40 ms to ensure with reasonable certainty that it can be met but that it is still low enough to indicate a time when the atria are relatively susceptible to defibrillation. This method may be combined with the first method, by programming a preset stability requirement A for a first time period; if A is not met during that first time period, the stability requirement for a subsequent time period is based on stability deltas calculated during the first monitoring time period.

As another alternative, the stability cycle length requirement may be set to take into account the average cycle length of the window being monitored. This is beneficial because windows with short average cycle lengths will likely have smaller absolute stability deltas than windows with longer average cycle lengths, without necessarily being more stable. The stability requirement may be set to be less than or equal to a certain percentage, preferably 5 to 20% and for example 10%, of the average cycle length of the window being monitored. For example, using 10%, a window with an average cycle length of 200 ms would have a stability requirement of 20 ms, while a window with an average cycle length of 150 ms would have a stability requirement of 15 ms. If the rhythm is stable, that is, if the stability cycle length requirement has been met, then a capacitor may be charged in preparation for shock delivery. Alternatively, the capacitor may be charged during any of the monitoring periods described above. As another alternative, if low voltage therapy is to be used, such as antitachycardia pacing, capacitor charging is not required. (If the rhythm is not stable, then the process is continued at step 40; see below.)

An additional criterion may be added that this stability be maintained over several sequential windows, as shown in FIG. 2B. A counter n is started at n=0 at step 34. A window of intervals is monitored at step 28*b*. A stability delta for the widow of intervals is calculated in step 30*b*. If the stability delta is less than the current stability requirement, counter n is incremented by one at step 36. If counter n is greater than or equal to a certain value, in this case 10 as shown in FIG. 2B at step 38, the process continues to step 40 on FIG. 2A. If counter n is less than 10, the process continues to step 46*b*. If the stability delta is not less than the current stability requirement, the counter is not incremented, and the process continues at step 34, resetting n=0. The number of sequential windows for which the stability delta must be less than the stability requirement may be reduced as time from AF detection increases. For example, if 10 windows were required when AF was first detected, after 30 minutes of AF at step 46*b* the number may be reduced to 5 at step 48*b*, and to only 1 after 60 minutes at step 50*b*.

As soon as an atrial interval is determined in step 40 to be between the second largest and second smallest interval of the current atrial window, the atrial defibrillation therapy is delivered in step 42. (The therapy may be ATP or a shock delivered synchronous with the next R-wave.) This ensures that the rhythm is still susceptible to defibrillation. If this requirement is not met and the current stability delta calculated in step 52 is still less than 20 ms as determined in step 54, the device will attempt to synchronize again on the next R wave.

Since delivery of atrial defibrillation may be many minutes from the onset of the arrhythmia, the criteria (i.e. amount of stability in cycle length) for defibrillation shock delivery may be different depending on how long the rhythm has persisted. In the initial period following onset of the arrhythmia, the criteria should be the most strict (i.e. very stable cycle lengths). If at step 46*a*, after a certain amount of time has elapsed, such as 30 minutes, and this criteria is not met, a less strict criteria (larger value for stability requirement or fewer sequential windows of stability or both) should be applied in step 56 if the elapsed time is less than 45 minutes at step 58. This less strict stability requirement B may be preprogrammed or may be based on the stability deltas observed in the initial period (in this case, 0 to 30 minutes). These parameters should be set such that they are likely to be met during the subsequent analysis period. That is, they should be less strict than the most stable period observed, and can be calculated as an offset from the values obtained during the initial period. If at step 58 after the time period of 30 to 45 minutes using the less strict stability requirement B, this criteria is not met, the next time period of 45 to 60 minutes following atrial arrhythmia detection as determined at step 50*a* uses another stability criterion—stability requirement C—set in step 60 either preprogrammed or based on the amount of stability seen in the 30 to 45 minute time period. If this criterion still is not met at 60 minutes in step 50*a*, a defibrillation shock can be delivered at 60 minutes, synchronous with the R wave, but disregarding atrial cycle length information.

Any standard method for sensing the atrial signal for interval calculation can be employed. It is well-known in the art for pacemakers and defibrillators to determine cycle length (i.e. interval) as the time between two cardiac events, where each event is denoted as when the electrical signal exceeds a given voltage threshold within the device. The threshold is determined by the device, and can be based on the characteristics of previous events. Some examples of thresholding that may be used include fixed or exponential decay.

The interval calculation can be derived from various atrial signal sources or any combination of bipolar and unipolar electrodes on which an atrial signal can be seen. The preferred embodiment uses a filtered atrial signal (either bipolar or unipolar), because the signal would be less likely to be corrupted by far field signals. Also, since the algorithm is based on timing (e.g. cycle length), a signal with a higher slew rate (more typical of a local, smaller electrode signal) provides a more consistent cycle length when the signals are regular. However, the possible advantage of a more global signal (e.g. far-field) is that the stability of the entire atrium may be quantified by the stability delta. More than one atrial signal can be used in determining the time of optimal shock delivery. In one embodiment of the invention, two signals may be used in determining the timing of optimal shock delivery, with the stability deltas of both having to meet the current stability requirement prior to therapy delivery; then, after a certain amount of time has passed since AF detection without both signals meeting the requirement, only one of the two signals is required to meet the stability requirement prior to therapy delivery.

If the delivered defibrillation therapy is below the pain threshold of the patient, multiple attempts can be made. If the first attempt using the above outlined method were unsuccessful, another attempt could be made with the same therapy, but at a different time offset from the atrial depolarization. This is essentially "scanning" the P wave, in hopes of breaking the circulating wavefront. This is similar in principle to antitachycardia pacing (ATP).

Alternatively, if the therapy delivered at step 42*a* were unsuccessful yet painless to the patient, the stability requirement could be made more strict to increase the likelihood that the next delivery of the same painless therapy is successful. Following redetection of AF at step 44*a*, a more strict stability requirement, A', is set at step 64 in FIG. 2C. A window of intervals is monitored at step 28*c*. A new stability delta is calculated for the window at step 30*c*. If the stability delta is less than the stability requirement at step 32*c*, the same painless therapy is delivered again at step 42*c*. If the therapy is not successful and AF is redetected at step 44*c*, the device will switch to a different or more aggressive therapy and/or a more strict stability requirement at step 66. The different or more aggressive therapy may have a different waveform or magnitude, may be a shock instead of ATP, or may be delivered using different electrodes from the first therapy.

In FIG. 2A, the stability requirement was loosened in steps 56 and 60 in response to time passing since detection of AF without meeting the more strict stability requirement A. It should be noted that one alternative to loosening the stability requirement is to decrease the width of the window (number of intervals) monitored in step 28a for which the stability delta is calculated. The number of intervals may, for example, start at 10 and be reduced to 5 after a certain amount of time has passed without meeting the stability requirement using 10 interval windows. In FIG. 2C, a similar loosening of the stability requirement in response to time passing since AF detection without meeting the more strict stability requirement A' occurs at step 68.

Figure 3:
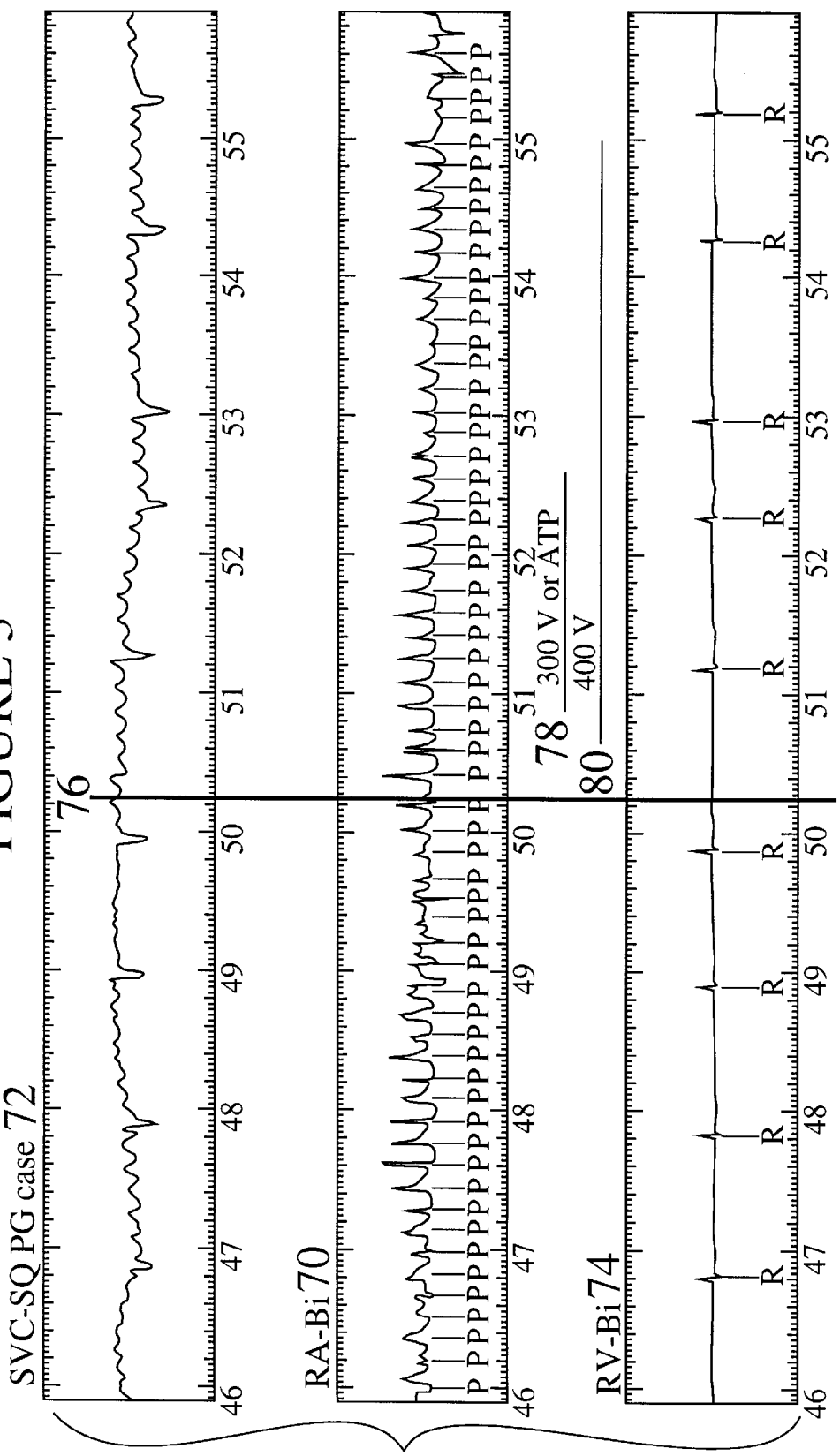
FIG. 3 shows a simulated electrogram during AF.

FIG. 3 shows a simulated near-field electrogram 70 and far-field electrogram 72 from the unipolar and bipolar pairs of sensing electrodes in FIG. 1, respectively, and a ventricular bipolar electrogram 74, during atrial fibrillation. The tracings show transition 76 from a disorganized atrial fibrillation to a more flutter-type atrial arrhythmia. The periods susceptible to defibrillation, 78 and 80, are shown along the time axis for a 300 V and a 400 V shock, respectively, and correspond to a maximum stable AF cycle length, which varies with the defibrillation shock strength. As shown, a 400 V shock would have a larger window and/or more windows of susceptibility to defibrillation than would a 300 V shock. Also, during the most flutter-like rhythms, atrial ATP may be used to terminate the arrhythmia. If this were to fail, a shock could be delivered.

In addition to the sensing electrode configuration shown in FIG. 1, which allows use of tip electrode 14 and ring electrode 16 in the right atrium for near-field sensing, and an SVC defibrillation electrode 10 to an active pulse generator case 12 for far field sensing, sensing for timing may be accomplished using electrograms from other combinations of electrodes. Some of the possibilities are shown in FIGS. 4–7. Some electrode configurations may be better than others for determining the relative amount of depolarization of the heart, and the preferred configuration may be different for different patients.

Figure 4:
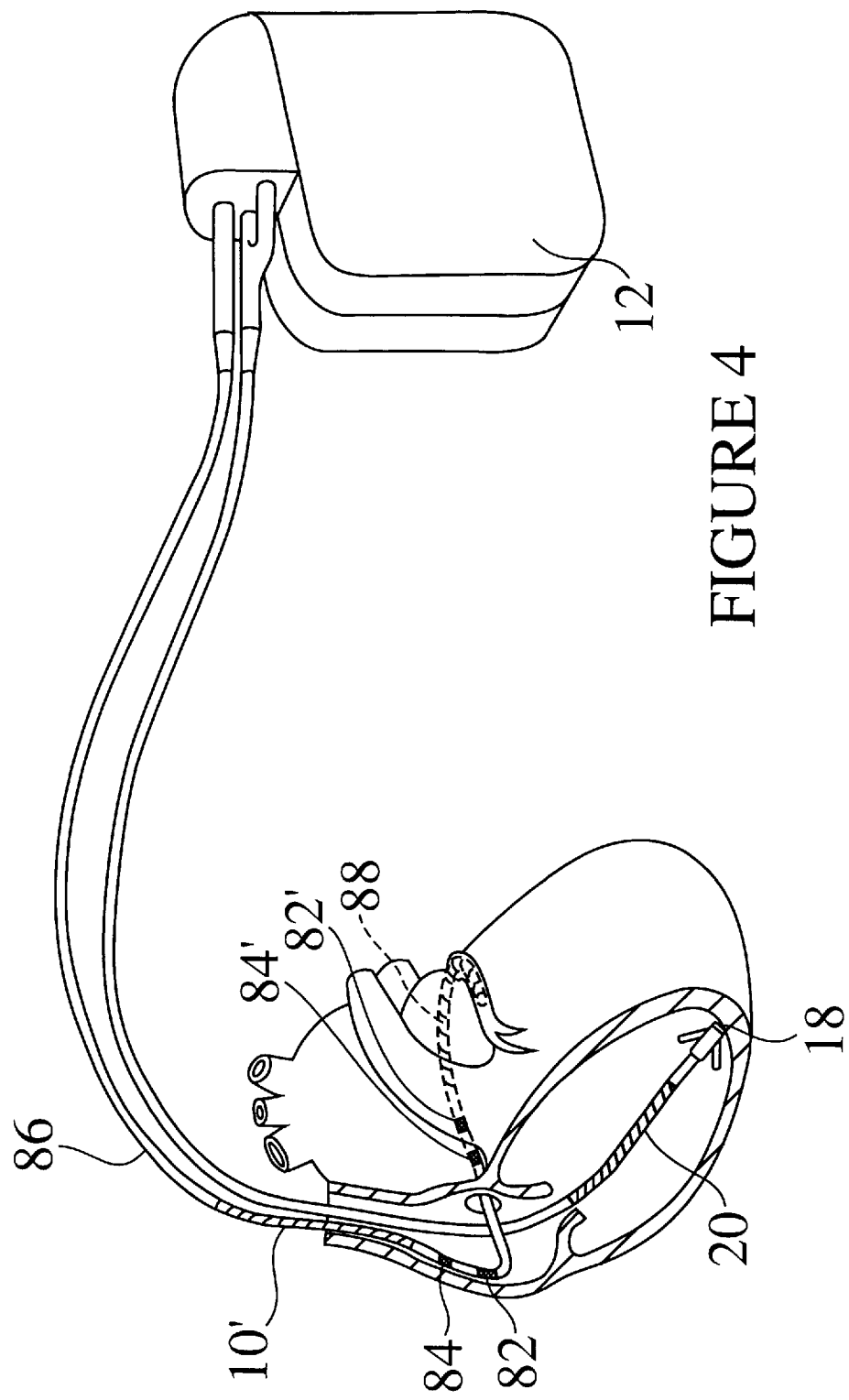
FIG. 4 is an illustration of an electrode system for sensing the near-field electrogram using closely-spaced bipolar ring electrodes.

FIG. 4 is an illustration of an electrode system for sensing the near-field atrial electrogram using closely-spaced bipolar right atrial ring electrodes 82 and 84 or coronary sinus ring electrodes 82' and 84' on a single-pass biatrial pacing lead 68. Also included on single-pass biatrial pacing lead 86 are defibrillation electrodes 10' and 88.

Figure 5:
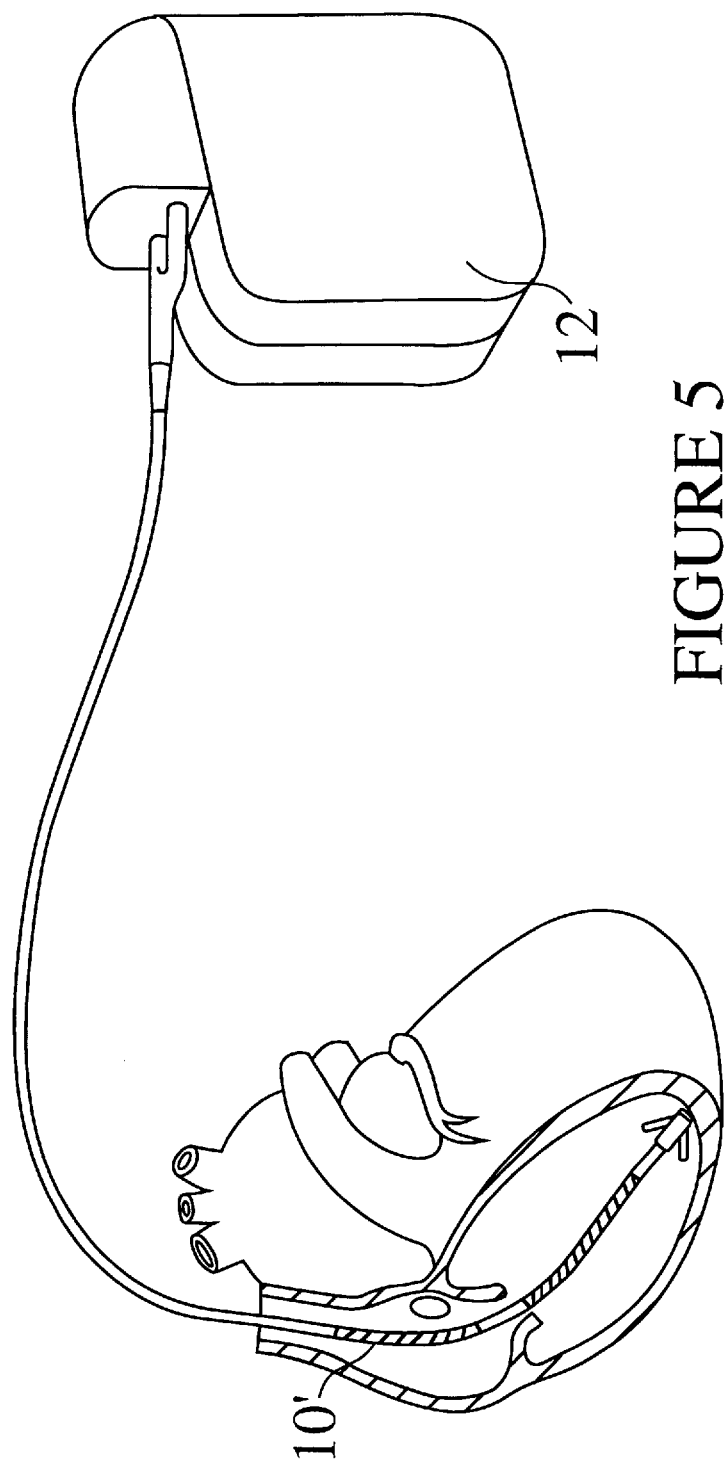
FIG. 5 is an illustration of an electrode system for sensing a more global (far-field) atrial electrogram from larger surface area electrodes.

FIG. 5 is an illustration of an electrode system for sensing a more global (far-field) signal electrogram from larger surface area electrodes, in this case, RA defibrillation electrode 10' to PG case electrode 12. An R wave suppression and/or subtraction algorithm is used to eliminate the ventricular signal in the information used to determine when the atria are more easily defibrillated, e.g., periods of stable cycle length.

Figure 6:
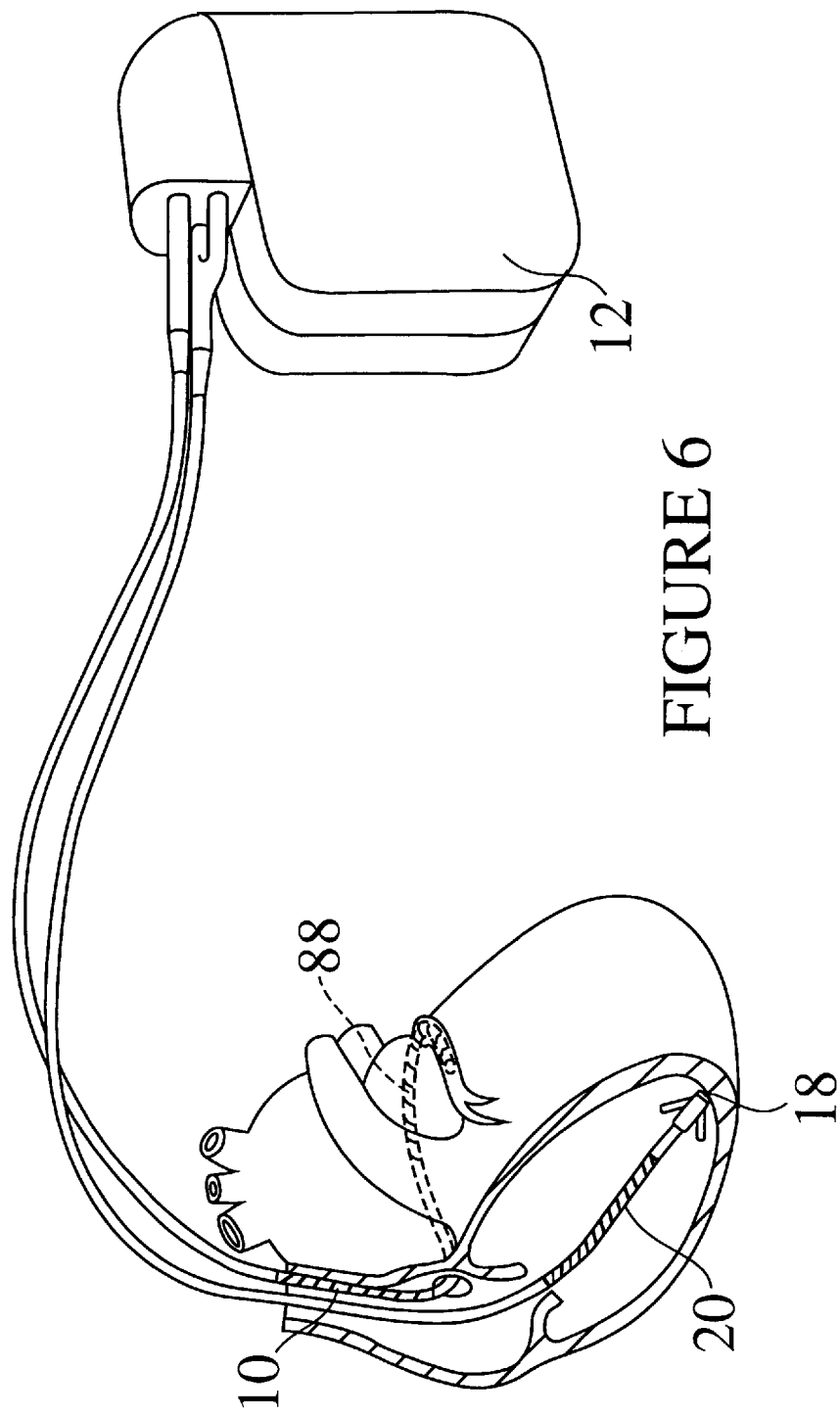
FIG. 6 is an illustration of an electrode system for sensing the far-field ventricular electrogram using a coronary sinus (CS) defibrillation electrode to RA defibrillation electrode.

FIG. 6 is an illustration of an electrode system for sensing the far-field atrial electrogram from a CS defibrillation electrode 88 to RA or SVC defibrillation electrode 10.

In an alternative embodiment, CS electrode 88 and SVC electrode 10 may form one sensing pair, and CS electrode 88 and SubQ electrode 12 may form a second sensing pair, thus producing two far-field ventricular electrograms. In this way, additional information is obtained regarding the direction of the fibrillation wavefronts, and vectorcardiography may be used to further determine the period during which a defibrillation shock will be most likely to successfully terminate fibrillation. Stability deltas may be obtained from several configurations, and a decision of when to deliver the shock can be made based on the results of them.

As an example of utilizing two AF signals, one bipolar (near field) and one "unipolar" (far field), consider the electrode configurations of FIG. 1, and the signals shown in FIG. 3. Both the cycle length of the bipolar signal and the cycle length of the unipolar signal are monitored. When the stability criteria are met in both signals, the level of organization in the heart is greatest, corresponding to the window of AF susceptible to defibrillation. The shock is delivered when the ventricles are not vulnerable to VF induction. Again, the optimum choice in timing may be patient-dependent.

Figure 7:
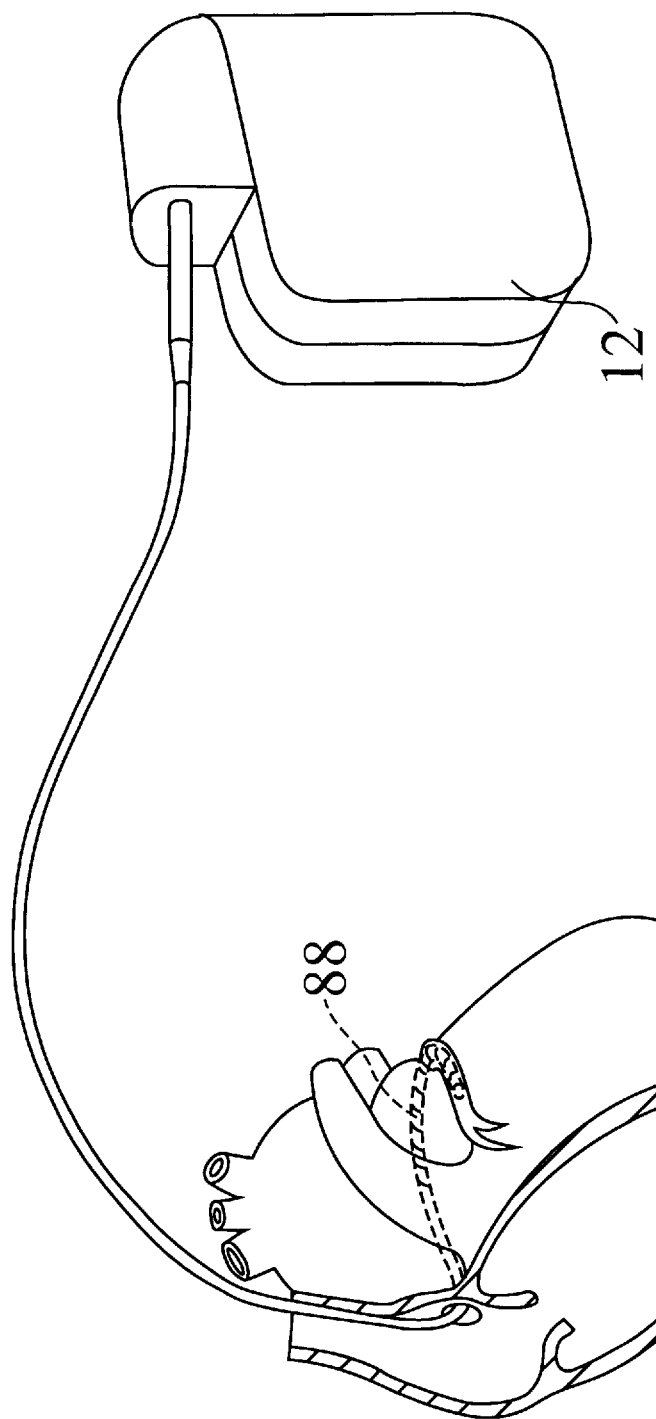
FIG. 7 is an illustration of an electrode system using a CS defibrillation electrode and an electrically active pulse generator housing to sense the far-field electrogram.

FIG. 7 is an illustration of using a CS defibrillation electrode 88 to a SubQ electrode 12, here shown as the electrically active pulse generator housing, to sense the far-field electrogram.

It should be understood that various alternatives to the embodiments of the invention described herein may be employed in practicing the invention. For example, this invention is not be restricted to high voltage shocks. High frequency burst pacing or other pacing techniques can be timed with the described window of AF susceptible to defibrillation. It is thus intended that the following claims define the scope of the invention and that structures and methods within the scope of these claims and their equivalents be covered thereby.

What is claimed is:

1. A method for defibrillating a patient's atria with an implantable defibrillator, comprising:
   (a) detecting atrial fibrillation in the patient's heart;
   (b) during a monitoring time period following atrial fibrillation detection, monitoring cycle length stability of at least one atrial fibrillation signal across first and second implanted electrodes;
   (c) comparing said cycle length stability to a preset stability requirement; and
   (d) delivering a first atrial defibrillation therapy when said cycle length stability meets said preset stability requirement.

2. The method of claim 1, wherein step (a) of detecting fibrillation includes sensing electrical signals using an electrode pair different from the pair formed by said first and second electrodes used to monitor atrial fibrillation in step (b).

3. The method of claim 1, wherein said step (b) comprises:
   (i) monitoring a window of between 8 and 20 cycles of atrial fibrillation;
   (ii) determining a second shortest cycle length and a second longest cycle length monitored during said window; and
   (iii) subtracting said second shortest cycle length from said second longest cycle length to obtain a stability delta, said stability delta being a measure of cycle length stability.

4. The method of claim 1 wherein said step (b) includes monitoring cycle length stability of at least one atrial fibrillation signal across an atrial ring electrode and an atrial tip electrode.

5. The method of claim 1, wherein step (b) of monitoring atrial fibrillation is carried out using a third electrode in addition to said first and second electrodes.

6. The method of claim 1 wherein said preset stability requirement in step (c) is between 5 and 80 ms.

7. The method of claim 1, wherein said atrial defibrillation therapy comprises antitachycardia pacing of said atria.

8. The method of claim 1, wherein said atrial defibrillation therapy comprises delivery of a defibrillation shock.

9. The method of claim 1, wherein step (d) of delivering atrial defibrillation therapy comprises delivery of a shock when the patient's ventricles are depolarizing.

10. The method of claim 1, wherein step (d) includes delivering atrial defibrillation therapy through at least one of said first and second electrodes used to monitor atrial fibrillation in step (b).

11. The method of claim 1, and further comprising the steps of:

(e) determining whether atrial defibrillation therapy delivered in step (d) was successful;

(f) if said therapy was unsuccessful, modifying said preset stability requirement to a more strict stability requirement;

(g) during a new monitoring time period following said unsuccessful therapy, monitoring cycle length stability of at least one atrial fibrillation signal across first and second implanted electrodes;

(h) comparing said cycle length stability to said more strict stability requirement; and (i) delivering a second atrial defibrillation therapy when said cycle length stability meets said more strict stability requirement.

12. The method of claim 11, wherein said step (i) includes delivering therapy of the same waveform and magnitude as said first atrial defibrillation therapy delivered in step (d) through the same electrodes used to deliver said first atrial defibrillation therapy in step (d).

13. The method of claim 11, wherein said step (i) includes delivering therapy of a different waveform from said first atrial defibrillation therapy delivered in step (d).

14. The method of claim 11, wherein said step (i) of delivering a second atrial defibrillation therapy includes delivering therapy of a different magnitude from said first atrial defibrillation therapy delivered in step (d).

15. The method of claim 11, wherein said step (i) of delivering a second atrial defibrillation therapy includes delivering therapy through different electrodes from said first atrial defibrillation therapy delivered in step (d).

16. The method of claim 1, wherein said step (c) includes comparing said cycle length stability to a preset stability requirement that varies according to the amount of elapsed time since detection of atrial fibrillation.

17. A method for defibrillating a patient's atria with an implantable defibrillator, comprising:

(a) detecting atrial fibrillation in the patient's heart;

(b) monitoring cycle length stability of at least one atrial fibrillation signal across first and second implanted electrodes during a first monitoring time period following atrial fibrillation detection;

(c) after said first monitoring time period, evaluating cycle length stability of said signal relative to said cycle length stability monitored during said first monitoring period during a second monitoring time period; and (d) delivering an atrial defibrillation shock during said second monitoring period when cycle length stability of said atrial fibrillation signal is within a desired measure of cycle length stability monitored during said first monitoring time period.

18. The method of claim 17, and further comprising:

(e) charging at least one high voltage capacitor in the implantable defibrillator during at least part of at least one of said first and second monitoring time periods.

19. The method of claim 17 wherein said step (b) includes monitoring cycle length stability during a time period from about 0 to about 30 minutes following the detection of atrial fibrillation of said step (a).

20. The method of claim 17, wherein step (b) further comprises monitoring a first of said fibrillation voltages using said first and second spaced apart electrodes and monitoring a second of said fibrillation voltages using said first and third spaced apart electrodes.

21. An implantable defibrillator, comprising:

a pulse generator;

atrial fibrillation sensing means;

sensing means for monitoring fibrillation cycle lengths during a monitoring time period following fibrillation detection;

electrode means for delivering a defibrillation shock during a period of atrial fibrillation when said fibrillation cycle lengths are within a desired measure of each other.

22. The implantable defibrillator of claim 21, further comprising:

a timer, wherein a shock is delivered through said electrode means upon timing out of said timer if said period of atrial fibrillation when said fibrillation cycle lengths are within a desired measure of each other has not been reached.

* * * * *